(12) United States Patent  (10) Patent No.: US 8,574,257 B2
Hamman  (45) Date of Patent: Nov. 5, 2013

(54) SYSTEM, DEVICE, AND METHOD FOR PROVIDING ACCESS IN A CARDIOVASCULAR ENVIRONMENT

(75) Inventor: Baron L. Hamman, Dallas, TX (US)

(73) Assignee: Edwards Lifesciences Corporation, Irvine, CA (US)

( * ) Notice: Subject to any disclaimer, the term of this patent is extended or adjusted under 35 U.S.C. 154(b) by 446 days.

(21) Appl. No.: 12/538,800

(22) Filed: Aug. 10, 2009

(65) Prior Publication Data

US 2010/0063363 A1  Mar. 11, 2010

Related U.S. Application Data

(63) Continuation-in-part of application No. 11/347,542, filed on Feb. 3, 2006, now abandoned.

(60) Provisional application No. 60/651,690, filed on Feb. 10, 2005.

(51) Int. Cl.
*A61M 29/00* (2006.01)
(52) U.S. Cl.
USPC .......................... 606/191; 606/108; 623/2.11
(58) Field of Classification Search
USPC .................. 606/184, 191–194, 197–199, 108
See application file for complete search history.

(56) References Cited

U.S. PATENT DOCUMENTS

| | | | |
|---|---|---|---|
| 958,854 A * | 5/1910 | Bunn | 604/267 |
| 3,143,742 A | 8/1964 | Cromie | |
| 3,320,972 A | 5/1967 | High et al. | |
| 3,371,352 A | 3/1968 | Siposs et al. | |
| 3,409,013 A | 11/1968 | Berry | |
| 3,546,710 A | 12/1970 | Shumakov et al. | |
| 3,574,865 A | 4/1971 | Hamaker | |
| 3,628,535 A | 12/1971 | Ostrowsky et al. | |

(Continued)

FOREIGN PATENT DOCUMENTS

| EP | 0 084 395 | 8/1986 |
|---|---|---|
| EP | 0 096 721 | 12/1987 |

(Continued)

OTHER PUBLICATIONS

Cardio Medical Solutions, Inc., "Baladi Inverter™, Clampless Surgery™," http://www.cardiomedicalsolutions.com, 1 page, Jan. 31, 2006.

(Continued)

*Primary Examiner* — Corrine M McDermott
*Assistant Examiner* — Alexander Orkin
(74) *Attorney, Agent, or Firm* — AnneMarie Kaiser; Guy Cumberbatch

(57) ABSTRACT

A device to be used in a cardiovascular environment, comprising an expandable element that is coupled to a rod and that includes a compressed state and an expanded state. The expandable element is operable to be positioned within a wall of an organ while the expandable element is in the compressed state. The expandable element is further operable to be deployed once it is within the organ such that it is in the expanded state. The device further includes a cutter element operable to make a circular incision at the wall of the organ. The expandable element creates a resistive force when it is pulled against the wall while in the expanded state such that an interface is created for making the incision. The device includes a stop-grip mechanism that maintains the resistive force at the interface. One embodiment features the expandable element being umbrella shaped.

19 Claims, 7 Drawing Sheets

(56) References Cited

U.S. PATENT DOCUMENTS

| | | |
|---|---|---|
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,664,114 A * | 5/1987 | Ghodsian .................. 606/193 |
| 4,680,031 A | 7/1987 | Alonso |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,917,097 A | 4/1990 | Proudian et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,540,658 A | 7/1996 | Evans et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,944,730 A | 8/1999 | Nobles et al. |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,371,983 B1 | 4/2002 | Lane |
| 6,402,780 B2 | 6/2002 | Williamson, IV et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,305 B1 | 10/2002 | Otte |
| 6,537,299 B1 | 3/2003 | Hogendijk et al. |
| 6,582,462 B1 | 6/2003 | Andersen et al. |
| 6,585,766 B1 | 7/2003 | Huynh et al. |
| 6,626,921 B2 * | 9/2003 | Blatter et al. .................. 606/153 |
| 6,635,068 B1 * | 10/2003 | Dubrul et al. .................. 606/200 |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,719,789 B2 | 4/2004 | Cox |
| 6,730,118 B2 | 5/2004 | Spenser et al. |
| 6,733,525 B2 | 5/2004 | Pease et al. |
| 6,764,508 B1 | 7/2004 | Roehe et al. |
| 6,767,362 B2 | 7/2004 | Schreck |
| 6,786,925 B1 | 9/2004 | Schoon et al. |
| 6,790,229 B1 | 9/2004 | Berreklouw |
| 6,790,230 B2 | 9/2004 | Beyersdorf et al. |

(56) References Cited

U.S. PATENT DOCUMENTS

| | | |
|---|---|---|
| 6,805,711 B2 | 10/2004 | Quijano et al. |
| 6,893,459 B1 | 5/2005 | Macoviak |
| 6,893,460 B2 | 5/2005 | Spenser et al. |
| 6,908,481 B2 | 6/2005 | Cribier |
| 6,918,908 B2 | 7/2005 | Bonner et al. |
| 6,939,365 B1 | 9/2005 | Fogarty et al. |
| 7,011,681 B2 | 3/2006 | Vesely |
| 7,025,780 B2 | 4/2006 | Gabbay |
| 7,070,616 B2 | 7/2006 | Majercak et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,422,603 B2 | 9/2008 | Lane |
| 7,513,909 B2 | 4/2009 | Lane |
| 7,556,647 B2 | 7/2009 | Drews et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0026238 A1 | 2/2002 | Lane et al. |
| 2002/0032459 A1* | 3/2002 | Horzewski et al. ........... 606/198 |
| 2002/0032481 A1 | 3/2002 | Gabbay |
| 2002/0058960 A1* | 5/2002 | Hudson et al. ................ 606/192 |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson, IV et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137609 A1 | 6/2005 | Guiraudon |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0246888 A1 | 11/2006 | Bender et al. |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |

(56) References Cited

U.S. PATENT DOCUMENTS

| | | |
|---|---|---|
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288089 A1 | 12/2007 | Gurskis et al. |
| 2008/0033543 A1 | 2/2008 | Gurskis et al. |
| 2008/0119875 A1 | 5/2008 | Ino et al. |
| 2008/0319543 A1 | 12/2008 | Lane |
| 2009/0036903 A1 | 2/2009 | Ino et al. |
| 2009/0192599 A1 | 7/2009 | Lane et al. |
| 2009/0192602 A1 | 7/2009 | Kuehn |
| 2009/0192603 A1 | 7/2009 | Ryan |
| 2009/0192604 A1 | 7/2009 | Gloss |
| 2009/0192605 A1 | 7/2009 | Gloss et al. |
| 2009/0192606 A1 | 7/2009 | Gloss et al. |

FOREIGN PATENT DOCUMENTS

| | | |
|---|---|---|
| EP | 0 125 393 | 12/1987 |
| EP | 0 179 562 | 7/1989 |
| EP | 0 143 246 | 11/1991 |
| EP | 1171059 | 1/2002 |
| GB | 2 056 023 | 3/1981 |
| GB | 2 069 843 | 9/1981 |
| GB | 2254254 | 10/1992 |
| GB | 2 279 134 | 12/1994 |
| SU | 1116573 | 7/1985 |
| WO | WO 89/00084 | 2/1989 |
| WO | WO 91/15167 | 10/1991 |
| WO | WO 92/01269 | 8/1992 |
| WO | WO 92/13502 | 8/1992 |
| WO | WO 92/19184 | 11/1992 |
| WO | WO 92/19185 | 11/1992 |
| WO | WO 95/17139 | 6/1995 |
| WO | WO 95/28899 | 11/1995 |
| WO | WO 96/40006 | 12/1996 |
| WO | WO 97/27799 | 1/1997 |
| WO | WO 97/09933 | 3/1997 |
| WO | WO 97/09944 | 3/1997 |
| WO | WO 99/15112 | 9/1997 |
| WO | WO 97/41801 | 11/1997 |
| WO | WO 97/42871 | 11/1997 |
| WO | WO 98/06329 | 2/1998 |
| WO | WO 99/11201 | 3/1999 |
| WO | WO 00/60995 | 4/1999 |
| WO | WO 99/51169 | 10/1999 |
| WO | WO 00/32105 | 6/2000 |
| WO | WO 00/40176 | 7/2000 |
| WO | WO 2006/086135 | 8/2006 |

OTHER PUBLICATIONS

Cardio Medical Solutions, Inc., "Baladi Inverter™, Clampless Surgery™," "Company Information," http://www.cardiomedicalsolutions.com/2.shtml, 1 page, Jan. 31, 2006.

E.K. Kerut, M.D., et al., "Left Ventricular Apex to Descending Aorta Valved Conduit: Description of Transthoracic and Transesophageal Echocardiographic Findings in Four Cases," Echocardiography: A Journal of CV Ultrasound & Allied Tech, vol. 18, No. 6, pp. 463-468, 2001.

D.A. Cooley, et al., "Apicoaortic Conduit for Left Ventricular Outflow Tract Obstruction: Revisited," The Society of Thoracic Surgeons, 4 pages, 2000.

J.D. Haines, Jr., et al., "Left Ventricular Apicoaortic Valved Conduit for Treating Obstruction of the Left Ventricular Outflow Tract," Southern Medical Journal, vol. 82, No. 6, pp. 756-757, Jun. 1989.

T.A. Vassiliades, "Off-Pump Apicoaortic Conduit Insertion for High-Risk Patients with Aortic Stenosis," European Journal of Cardio-Thoracic Surgery, pp. 156-158, Sep. 9, 2002.

C. Schreiber, et al., "Modified Bypass Procedure and Apicoaortic Conduit," Herz © Urban & Vogel, pp. 795-798, 2002.

A. Renzulli, et al., "Long-Term Results of Apico-Aortic Valved Conduit for Severe Idiopathic Hypertrophic Subaortic Stenosis," Apico-Aortic Prosthetic-Valved Conduit, vol. 27, No. 1, pp. 24-28, 2000.

M.S. Sweency, of al., "Apicoaortic Conduits for Complex Left Ventricular Outflow Obstruction: 10-Year Experience," The Annals of Thoracic Surgery, vol. 42, pp. 609-611, Dec. 1986.

J.W. Brown, et al., "Apicoaortic Valved Conduits for Complex Left Ventricular Outflow Obstruction: Technical Considerations and Current Status," The Annals of Thoracic Surgery, vol. 38, No. 2, pp. 162-168, Aug. 1984.

M.A. Ergin, et al. Experience with Left Ventricular Apicoaortic Conduits for Complicated Left Ventricular Outflow Obstruction in Children and Young Adults, "The Annals of Thoracic Surgery," vol. 32, No. 4, pp. 369-376, Oct. 1981.

J. Salas, et al. "Apicoaortic Conduit Implanted Without Cardiopulmonary Bypass: A Useful Contingency Technique," J. Cardiovasc Surg., pp. 798-800, 1989.

* cited by examiner

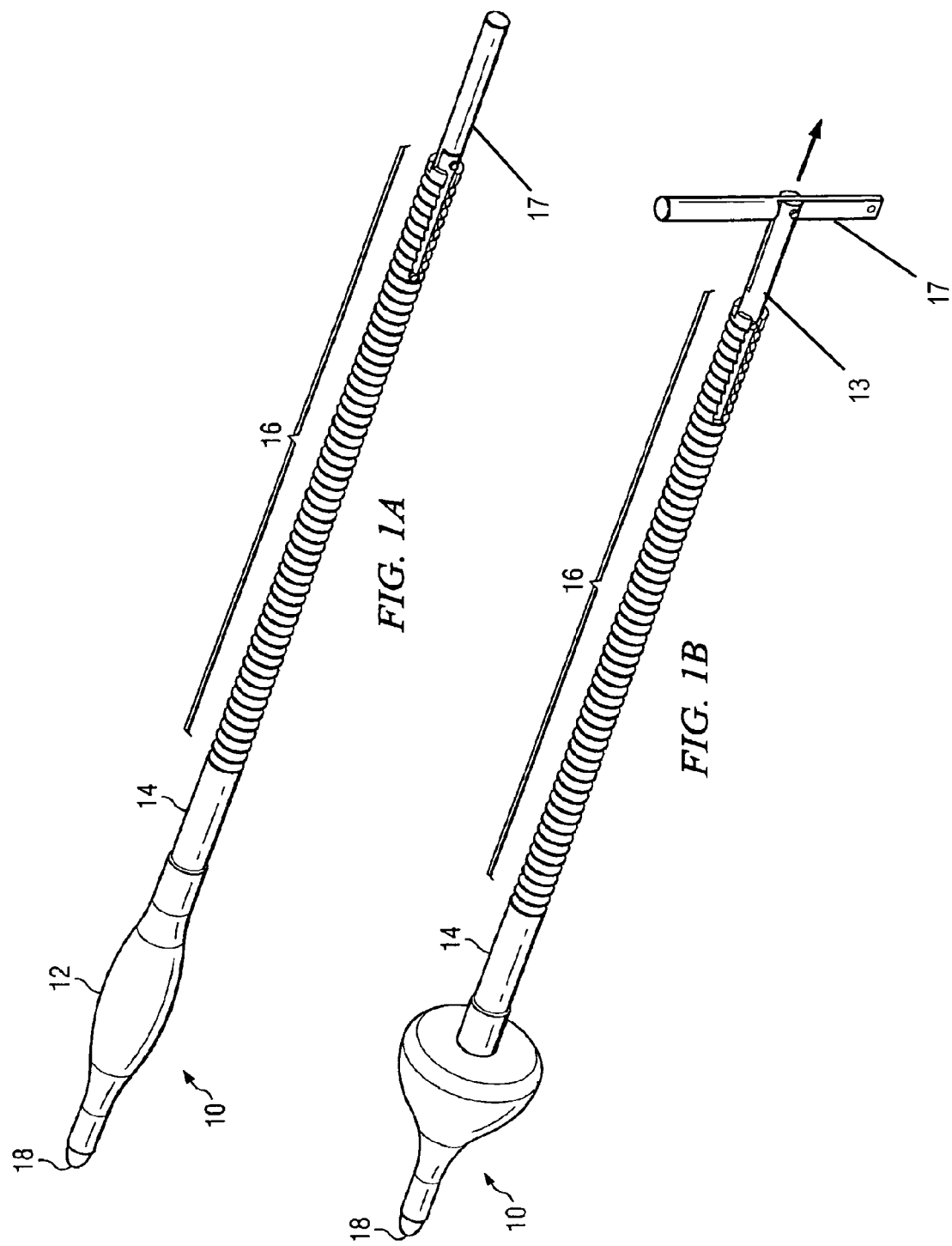

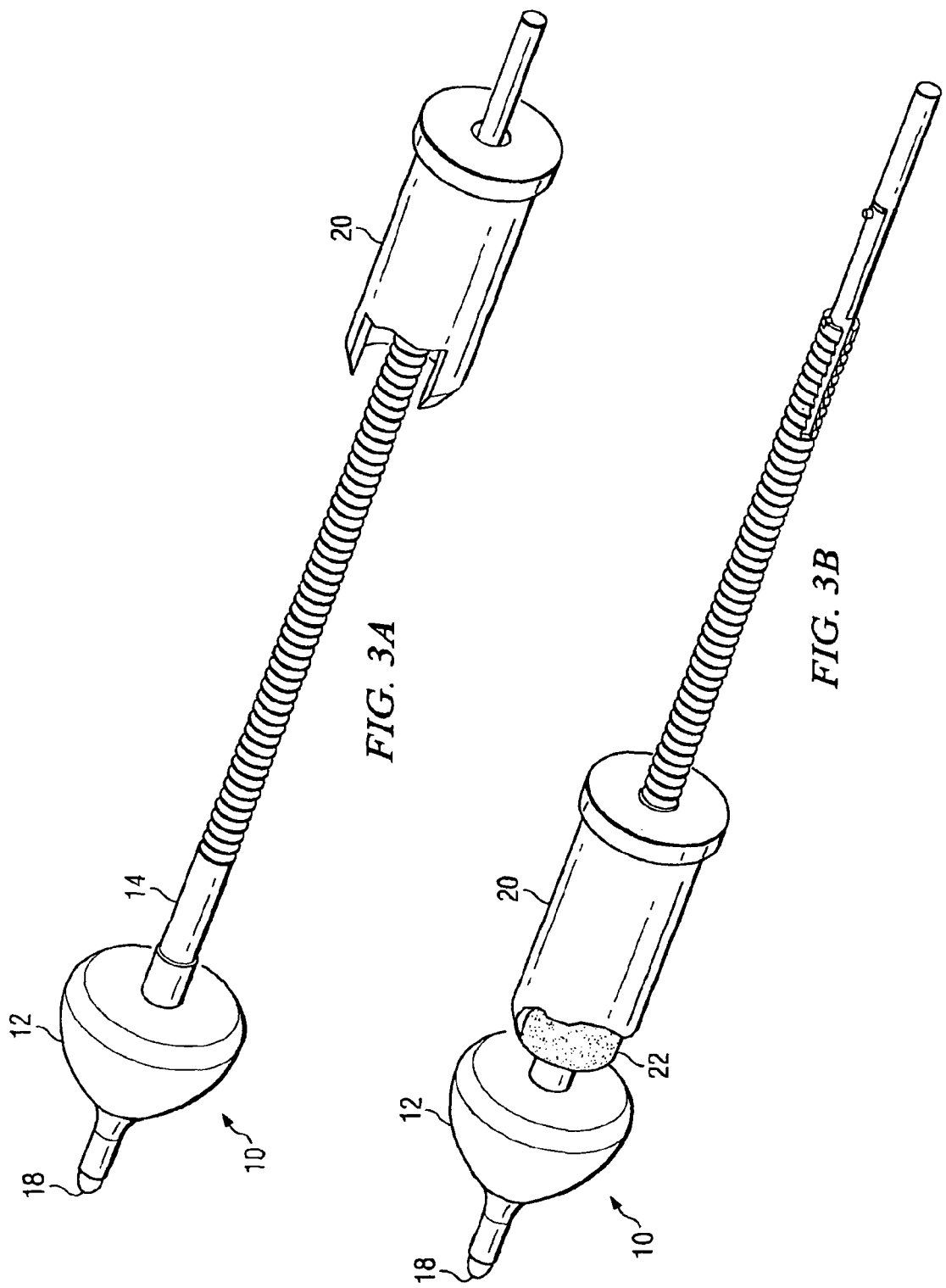

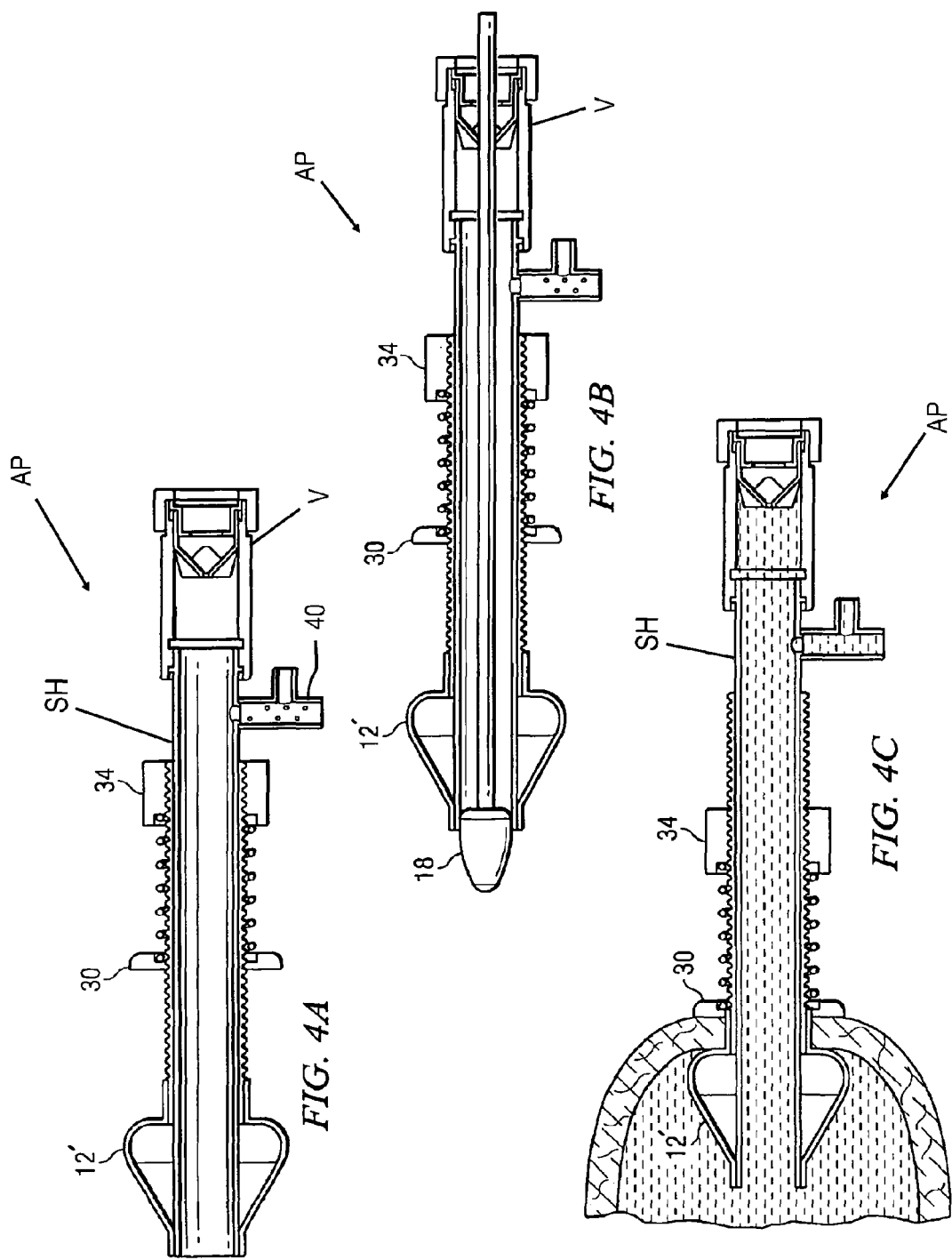

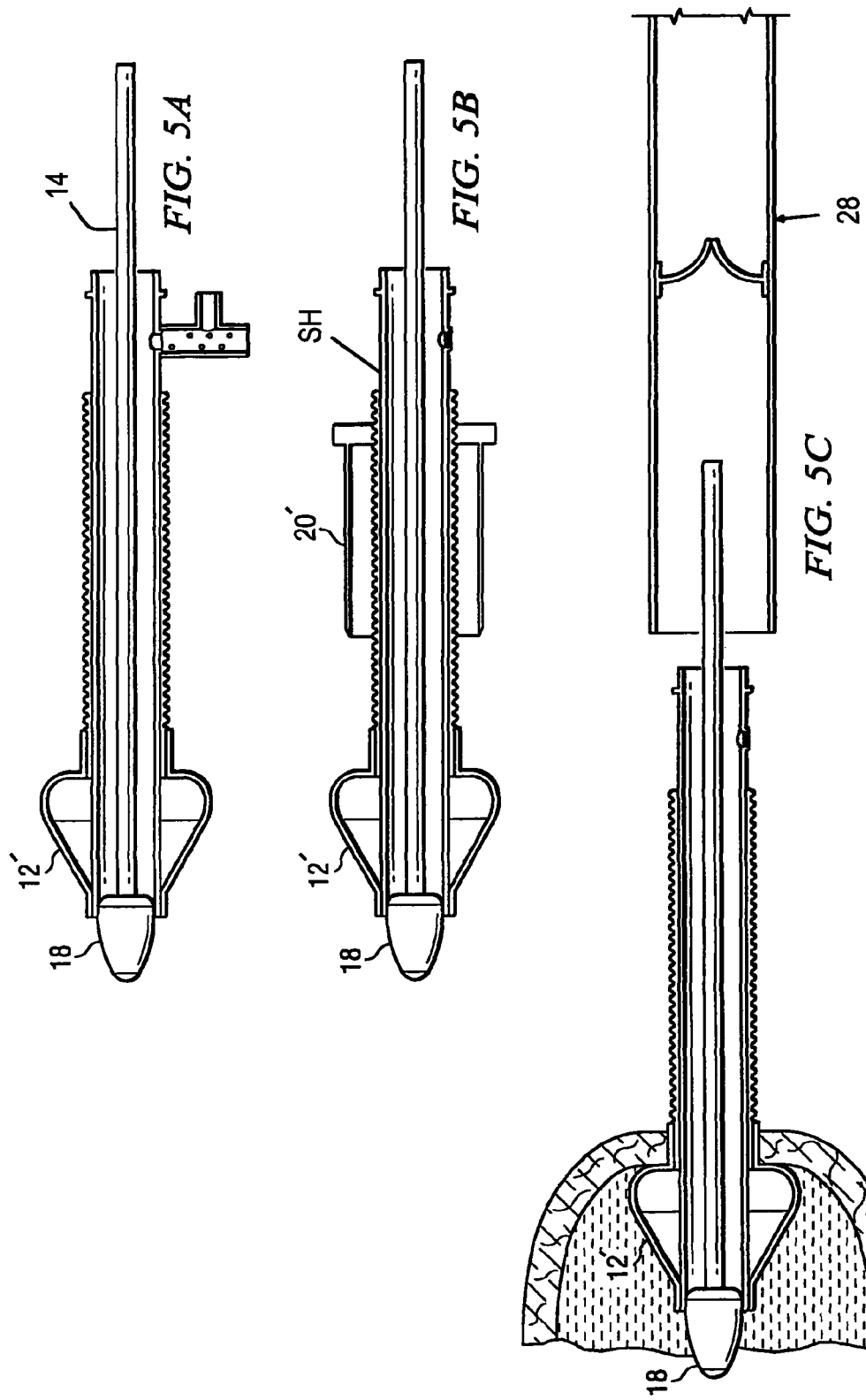

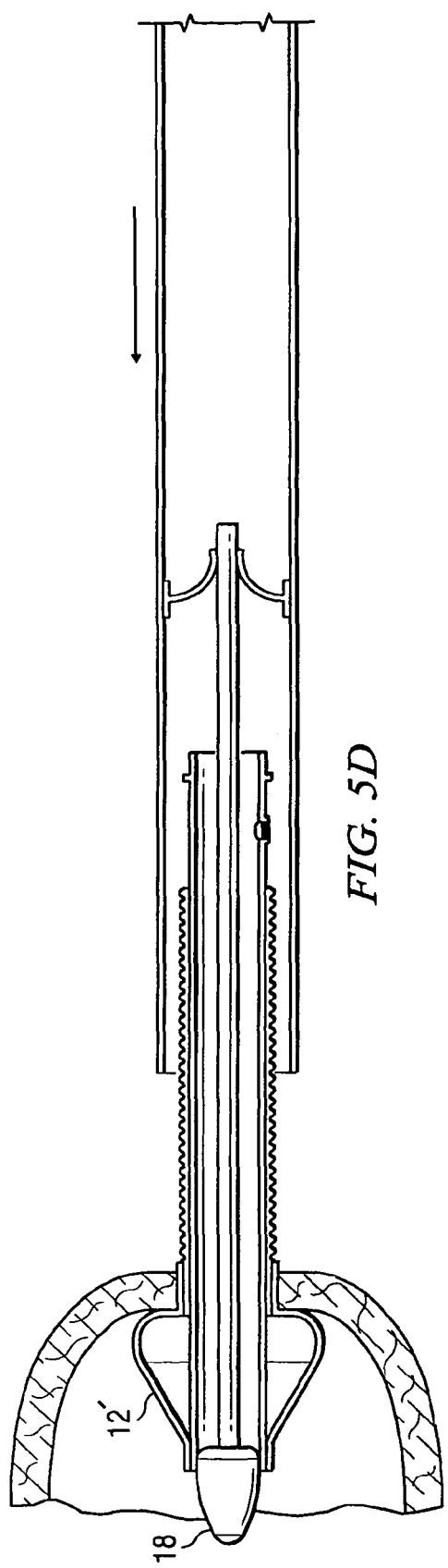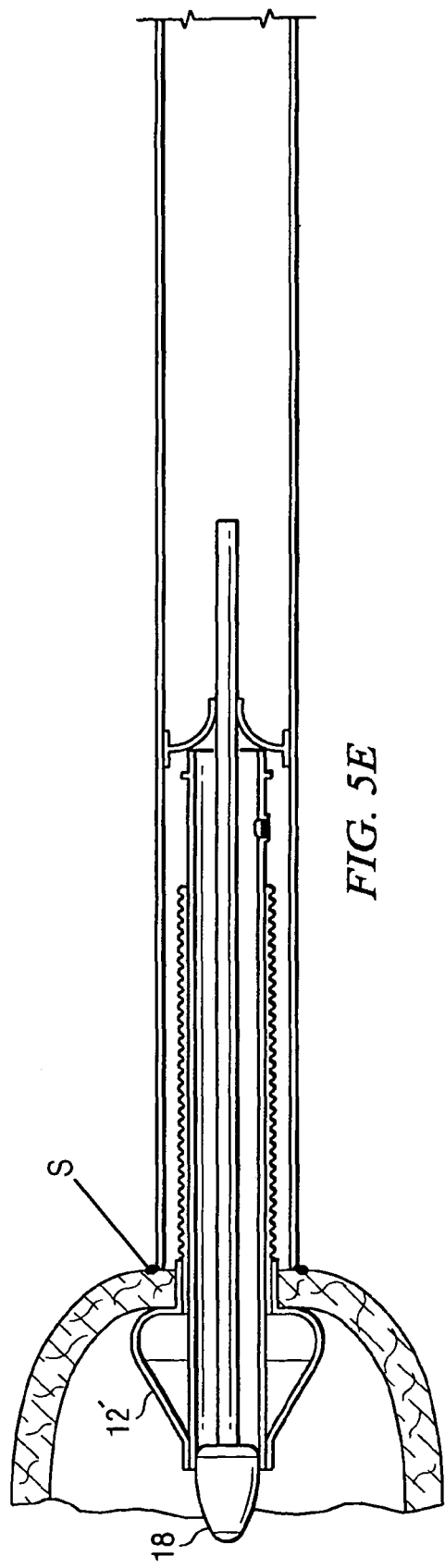

SYSTEM, DEVICE, AND METHOD FOR PROVIDING ACCESS IN A CARDIOVASCULAR ENVIRONMENT

RELATED APPLICATIONS

This application is a continuation-in-part of U.S. application Ser. No. 11/347,542, filed Feb. 3, 2006 and now abandoned, which claims priority under 35 U.S.C. §119(e) from U.S. Provisional Application No. 60/651,690, filed Feb. 10, 2005, both of which are incorporated herein by reference in their entireties.

FIELD OF THE INVENTION

The present invention relates to the field of cardiac and vascular surgery and, more particularly, to a system, a device, and a method for providing for access in a cardiovascular environment.

BACKGROUND OF THE INVENTION

The treatment of vascular diseases has grown exponentially in terms of sophistication and diversity. One area of interest relates to the ability to access the inside of the heart in order to touch, cut, move, paint, or burn areas of the heart in order to change its function, shape, conduction pattern, or to ablate a normal or an abnormal rhythm pattern.

Another area of interest pertains to the treatment of deficiencies in the heart and its chambers, valves, and vessels emanating therefrom. In certain cases of aortic stenosis or left ventricular outflow tract obstruction, surgeons have provided relief to patients by implanting a prosthetic valved conduit: extending from the apex of the left ventricle to the aorta. This conduit provides an outflow tract for flow exiting the left ventricle. The surgery leaves the natural outflow tract intact and untouched. This surgical technique has proven useful in cases of congenital or acquired supravalvular, valvular, and subvalvular stenoses where more conventional approaches (such as aortic valvotomy or commissurotomy) produce inferior results due to the severity of the obstruction. These substandard results may also be attributable to difficulties in affecting an accurate obstruction relief, or due to dropping debris from the attended valve (or other similar component). The debris can readily create an embolus that is free to travel with the blood flow and, potentially, cause a stroke (in the case of lodging in the brain) or other bodily injuries.

In more recent years, prosthetic conduits with valves have enjoyed substantial notoriety. Their popularity is due to their tremendous success rate, their efficacy, and their ability to offer extraordinary benefits to a patient.

Note that such cardiac procedures pose certain problems for a surgeon. For example, a surgeon is generally confined or restricted in his movements during the surgery, which may be due, in part, to instrumental limitations. A surgeon must often complete a number of sophisticated tasks during a given procedure. Some of these tasks should be completed somewhat concurrently or even simultaneously. Therefore, optimizing or simplifying any of these steps may yield a significant reduction in burden for a surgeon. Additionally, with the elimination of perfunctory tasks and tedious chores, the surgeon is then free to shift his attention where it is most needed: on the procedure itself.

Moreover, many surgical instruments that address issues at the apex of the heart are cumbersome, difficult to manipulate, potentially harmful to patients, and clumsy or awkward in many situations. Their deficiencies create a significant challenge for the surgeon, who is already being taxed by a number of arduous tasks. In addition, many current devices are unacceptable because they cause trauma and inflammation issues for the patient or because they have a propensity to cause strokes.

Accordingly, the ability to provide an effective medical instrument that properly accounts for the aforementioned problems presents a significant challenge for component manufactures, system designers, and surgeons alike.

SUMMARY OF THE INVENTION

From the foregoing, it may be appreciated by those skilled in the art that a need has arisen for an improved instrument for achieving superior control, management, and performance during a procedure that offers optimal access at a targeted surgical site. In accordance with an embodiment of the present invention, a device, a system, and a method for enhancing an operation involving access (particularly, but not limited to, left ventricular access) are provided that includes a flexible, highly precise, easy-to-use device, which substantially eliminates or greatly reduces disadvantages and problems associated with conventional equipment and instruments.

A device to be used in a cardiovascular environment, comprising an expandable element that is coupled to a rod and that includes a compressed state and an expanded state. The expandable element is operable to be positioned within a wall of an organ while the expandable element is in the compressed state. The expandable element is further operable to be deployed once it is within the organ such that it is in the expanded state. The device further includes a cutter element operable to make a circular incision at the wall of the organ (while sealing the intraorgan fluids inside). The expandable element creates a resistive force when it is pulled against the wall while in the expanded state such that an interface is created for making the incision. The device includes a stop-grip mechanism that maintains the resistive force at the interface (to allow unhanding of the device).

In a particular embodiment, the device is of a size sufficient to allow a sealed access to a cavity of the organ for placement, manipulation, or repair of a heart valve. A handle (e.g. an angulated rod handle) can be used to manipulate (and potentially lock) the expandable element into its compressed state and the expanded state.

Certain embodiments of the present invention may provide a number of technical advantages. For example, the present system can include a simple locking mechanism for maintaining a position of the device. The locking mechanism allows a surgeon to unhand the device and, thereby, offers exceptional flexibility and adaptability for a surgeon. Moreover, the operation of the device allows the port to be "dropped" back into the chest (i.e. not directly handled by the operator), while another device or tool is being readied for use. Still other advantages of the device would include minimizing blood loss during intra-ventricular surgical repair, while maintaining a pathway to minimize time during tool changes. The device allows for a number of beating heart surgeries to occur and, further, avoids the complications associated with heart-lung machines.

In addition, the present invention offers increased accuracy for a surgeon, who is relegated the difficult task of making a precise circular incision in the wall of the heart. Additionally, the device can access and seal a variety of ventricular or cardiac tissue walls.

Also, the proposed platform would allow a surgeon to insert a valve (or some other implantable device) through the interior of the port although it is not actually part of the implantable device. Additional details relating to these advantages are described below with reference to corresponding FIGURES.

Certain embodiments of the present invention may enjoy some, all, or none of these advantages. Other technical advantages may be readily apparent to one skilled in the art from the following figures, description, and claims.

BRIEF DESCRIPTION OF THE DRAWINGS

To provide a more complete understanding of the present invention and features and advantages thereof, reference is made to the following description, taken in conjunction with the accompanying figures, wherein like reference numerals represent like parts, in which:

FIGS. 1A-1C are simplified schematic diagrams that illustrate a top view of a device to be used in a surgical procedure in accordance with one embodiment of the present invention;

FIGS. 3A-3B are simplified schematic diagrams of a top view of the device in which a cutter element is provided thereon;

FIGS. 4A-4C are simplified schematic diagrams of a top view of the device in combination with a tube that facilitates various operations of the device; and FIGS. 5A-5G are simplified schematic diagrams of example configurations of the device in which various portions of the device have been removed.

DETAILED DESCRIPTION OF THE PREFERRED EMBODIMENTS

Currently, there are few relevant devices available on the market for solving a number of problems associated with beating heart left ventricular (or intracardiac) access. Generally, interventions require surgical skill to perform placement of the valved conduits. Access to the ventricle has previously been established by cutting a linear incision and by performing a dilation of the linear incision in order to gain access. The linear incision is then subsequently repaired by sutures. The systems described herein offer improved designs and provide an instrument capable of readily accessing the interior chamber of the heart: providing a hemostatic sealed port for introducing tools into the interior chamber of the heart.

Generally, an access port system described herein can be used in conjunction with any other system to provide access to the ventricle, to the atrium, or to any large intracardiac or intravascular structure while the heart is still beating and may or may not be pumping blood. In specific applications, the access port system could be used as an access port for mitral or aortic valve manipulation, replacement, repair, or for atrial fibrillation procedures or ventricular wall geometric procedures.

In alternative embodiments, or in case an initial surgery proves unsuccessful, the present system can serve as a chassis for mounting a valved conduit. The valved conduit system could allow therapy for patients who are not candidates for traditional therapies such as cardio pulmonary bypass, or for patients having aortic calcification or calcified stenosis of the valves.

Before proceeding further, for purposes of teaching and discussion, it is useful to provide some overview as to one way in which the following invention operates. The following foundational information may be viewed as a basis from which the present invention may be properly explained. Such information is offered earnestly for purposes of explanation only and, accordingly, should not be construed in any way to limit the broad scope of the present invention and its potential applications.

Figure 2:
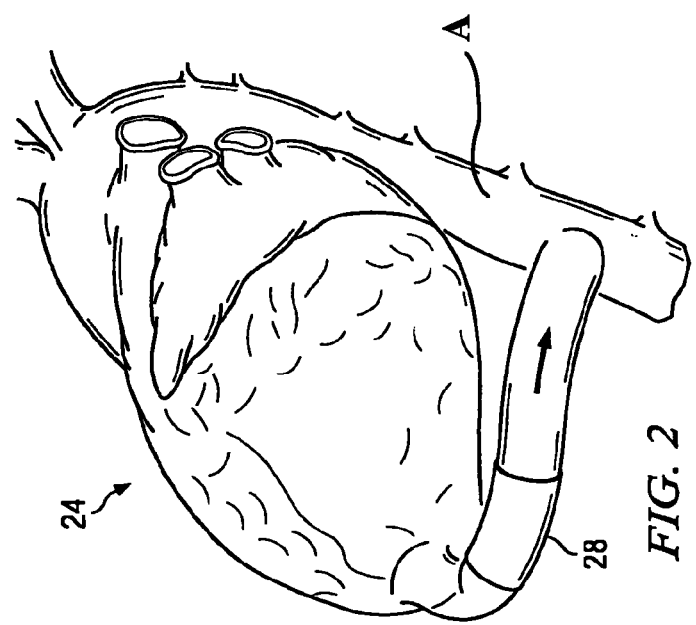
FIG. 2 is a simplified schematic diagram of a heart and a valve conduit, which are representative of a scenario in which the device of FIG. 1 may be applicable.

An exemplary environment in which the present system can operate is illustrated by FIG. 2. FIG. 2 is a simplified schematic diagram that illustrates a heart 24, which includes a valve conduit system 28 connected to the descending aorta A. An arrow is illustrated as showing blood flow from the apex of heart 24 to the aorta A. Many existing systems attempt to achieve relief of an obstruction to the outflow of the left ventricle by opening or replacing the aortic valve. The aortic valve location has previously been a popular choice because it is a somewhat "natural" solution to employ. However, incising a hole in the apex of the heart (i.e. at the bottom of the heart) is also a viable solution. Thus, instead of pumping out of the aortic valve, which may be diseased, narrowed, or somewhat occluded, a suitable outflow can be achieved at the bottom of the heart through a hole and, subsequently, an implantable valve that facilitates one-way blood flow can be used. Hence, the apex of the heart could readily be used for placement of a valve conduit. However, such a procedure is not without its flaws, for example this paradigm is generally considered to be cluttered and somewhat messy.

Aside from the aforementioned procedural flaws, there are also a number of additional issues that a surgeon should be aware of in attempting to incise a hole at the apex of the heart. For example, one problematic issue in such an environment involves the use of a cardiopulmonary bypass pump. Another problematic issue relates to clamping of the aorta. Inherent in both of these issues is the potential for strokes. The present invention solves these issues, and others, by enabling off-pump surgery and providing a flexible access port which would keep much of this clutter out of the surgeon's way.

Figure 1C:
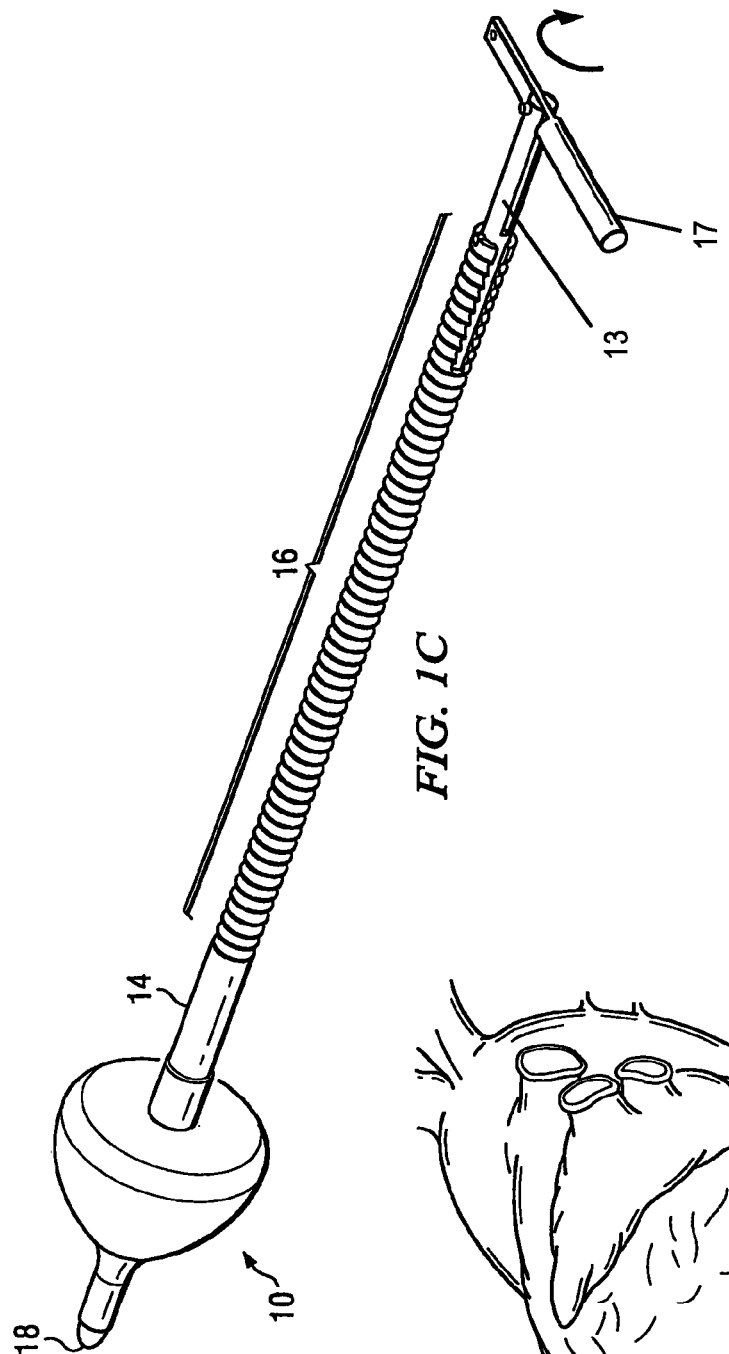

FIGS. 1A, 1B, and 1C are simplified schematic diagrams that illustrate an entry device 10 for creating an effective point of entry at a targeted location. In one embodiment, the targeted location is the apex of the heart. However, the targeted location can be any other suitable location in the body in which a small piece of tissue is sought to be removed by a surgeon or where a sealed access to a fluid or gas containing organ is desired. Device 10 includes an expandable element 12 (which is umbrella shaped in one embodiment) connected to a rod 13 that translates within a shaft 14 which includes a threaded portion 16. Device 10 also includes an obturator 18, which is olive shaped and which facilitates a smooth streamlined entry for the attending surgeon. Furthermore, obturator 18 and shaft 14 may be utilized to provide an inner fluid seal within a larger tubular access port AP as described below. In one embodiment, obturator 18 is blunt at its end such that it does not pierce a valve (or other delicate structure) that may be subsequently placed, removed, burned, ablated, or manipulated by the surgeon. Obturator 18 does have enough sharpness or rigidity such that it accomplishes some directionality. In an alternative embodiment of the present invention, obturator 18 may be replaced by any other suitable element that facilitates an efficient entry at the targeted location for the surgeon.

Additionally, obturator 18 may be coupled to an accompanying handle for purposes of actuation, as is illustrated in FIG. 1C. Thus, an angulated rod handle driver, including the rod 13 with an accompanying pin structure 17, can be provided to device 10. A sleeved locking mechanism may be used to manipulate expandable element 12 to either its compressed or its expanded state. Specifically, FIG. 1A illustrates the handle in an inactive mode such that expandable element 12 is in a collapsed state, whereas FIG. 1B illustrates device 10 where the handle is being displaced proximally to pull obturator 18 and deploy expandable element 12. FIG. 1C illustrates the handle being used to further deploy expandable element 12 such that the umbrella is fully expanded. To deploy the expandable element 12, therefore, the user retracts the handle driver until the element expands, and then locks it in the expanded configuration by rotating the pin structure 17.

Expandable element 12 and shaft 14 are constructed of a hard plastic material in one embodiment. In other embodiments, expandable element 12 and shaft 14 are constructed of any suitable polymer or composite material. These elements may be coupled to each other in any appropriate fashion, or these items may simply be integral. Alternatively, the design of device 10 may be changed, enlarged, or modified considerably in order to accommodate particular arrangements or configurations. The illustrated examples of FIGS. 1A and 1B can be altered considerably without departing from the broad teachings of the present invention.

In one embodiment, expandable element 12 has a diameter of approximately 18-30 mm in the expanded state (FIG. 1C) and 8-12 mm in diameter in the initial collapsed configuration (FIG. 1A). When deployed, expandable element 12 is preferably larger than a hole cutter (which is described in greater detail below) by about 2-8 mm in diameter (or greater or less, depending upon particular applications) to allow for stability of the system after the cutter removes a concentric circular piece of tissue.

Device 10 can leverage expandable element 12 (or any other collapsible item that can provide the requisite seal) to provide for stabilization and, further, to produce a hemostatic effect on the interior of the heart. For an introduction at the surgical site, expandable element 12 of device 10 is in its collapsed state with the deployable member at its minimum profile over the shaft (e.g. 10 to 14 mm diameter).

The shaft 14 of device 10 initially has a dilator positioned within an inner lumen which extends out from the distal tip of device 10. The surgeon can make a small cut in the wall of the heart at the desired location for the access port. Device 10 is then inserted through the wall of the heart and when expandable element 12 is fully within the heart, the inner rod 13 of device 10 is manipulated relative to the shaft 14 to deploy the expandable member. The dilator can be removed so that access through the wall is permitted.

As highlighted above, expandable element 12 can be a braid, a balloon, a malecot, or any other suitable component that is capable of being collapsed from its original state to a smaller state for introduction into the targeted site. Once suitably positioned or installed, expandable element 12 can then be deployed such that it occupies a larger diameter. This maintains its position and provides a natural hemostasis.

For example, a braid (that serves as expandable element 12) can be used in such an arrangement, which can be shaped to provide an optimal sealing against the interior heart chamber. The braid could be coated with an elastomeric membrane (e.g. such as silicone or polyurethane) to provide a sealed surface. Device 10 may be made with a dense enough braid or fiber structure to allow the fibers alone to provide suitable resistance to the passage of blood.

FIGS. 3A and 3B are simplified schematic diagrams that further illustrate a cutter element 20 of device 10. Cutter element 20 has a certain sharpness such that it is operable to incise a hole that is smaller than expandable element 12. Cutter element 20 is somewhat hollow or concave such that it can incise a hole and retain the incised portion of tissue. The incised portion would be of a doughnut shape and, further, could be used for the purpose of biopsy where appropriate.

Once the tissue has been effectively removed, then the surgeon could position a valve conduit (e.g. with self-attaching legs) in the hole and secure the valve. Once the valve is properly secured, then expandable element 12 is undeployed or collapsed and subsequently removed. A completed connection of a valve conduit 28 was described above with reference to FIG. 2.

Cutter element 20 engages shaft 14 through threaded portion 16 such that rotation of cutter element 20 causes it to move toward expandable element 12. In other embodiments, cutter element 20 may move along shaft 14 in any suitable fashion (e.g. spring loaded mechanisms, ratcheting configurations, notching arrangements where shaft 14 is designed to include specific locations at which cutter element 20 can be secured, simple cam configurations, etc.).

In operation of an exemplary procedure, device 10 is generally pulled to seat the expandable member against the inner surface of the heart. At this point, cutter element 20 is installed onto the shaft and advanced down to the heart wall. As mentioned above, cutter element 20 may ride on any suitable mechanism such as a thread or a cam (or any other suitable advancing mechanism), which advances the cutter. Additionally cutter element 20 has a distal sharpened end, which cuts tissue as it is rotated or advanced into the tissue. Cutter element 20 also may include a tissue retaining feature such as an interior ridge or internal barbed spikes that retain the cut tissue in the cutter. In this one non-limiting example embodiment, cutter element 20 is in a range of 13 to 25 mm in diameter.

After cutting and removing the circular tissue, continued traction on the expanded braid 12 maintains hemostasis of the hole. A heart valve and vascular conduit (such as seen as the valve conduit system 28 in FIG. 2) can then be installed over the shaft of the device 10 and positioned into the cut hole in the heart. This conduit can be attached to the heart via suturing or other suitable methods where appropriate. With the valve and conduit installed and sutured to the heart, the expandable member can be released and hemostasis of the valve and heart attachment verified. Once the valve placement is verified, and the surrounding area is sutured and sealed, the expandable member can be collapsed and then gently removed from within the valve and conduit. Finally the conduit can be attached to the aorta or other suitable structure and the final anastomosis completed.

Specifically, the present invention can utilize an umbrella-shaped design, whereby device 10 can be easily inserted into (and removed from) the target location in a collapsed state. In a compressed or collapsed state, device 10 is generally small in relation to the incised hole. Once suitably positioned, device 10 can be deployed, where it is free to expand. By pulling back on device 10, the umbrella design can expand to an area greater than the incised hole. Hence, the surgeon can stabilize the environment by simply creating enough pressure between device 10 and the wall of the heart.

Such an arrangement is ideal, as it offers tremendous freedom and maneuverability for the surgeon. With device 10 suitably positioned, the surgeon is free to sew in a valve conduit, or any other device, at this surgical location. Once the valve conduit (or any other element) is sewn, then the umbrella portion of device 10 can be undeployed (i.e. collapsed) and removed from the site.

One advantage provided by device 10 is that it is capable of making a circular cut that approximates a valve conduit (or any other element sought to be placed at the surgical site). A circular cut is important for achieving a superior seal. Device 10 also augments flexibility and convenience for a surgeon because it is capable of locking into place once it is suitably positioned.

FIGS. 4A-4C are simplified schematic diagrams illustrating a top view of an access port AP used for an initial surgical procedure. As an overview, it should be understood that, although sharing some of the same features, FIGS. 4A-5C illustrate significant modifications in scale and in configurations as compared to the embodiments of FIGS. 1A-1C and 3A-3B. For example, the width of access port AP in FIG. 4A (at its widest point) is approximately 30-35 millimeters. Alternatively, based on one particular set of design choices, the width of the access port is only about 0.5 millimeters, which is unsuitable for passing larger instruments. It should be noted that specific measurements provided are only offered as examples, as any permutations or alterations in these specifications are clearly within the broad scope of the present invention. Accordingly, these measurements should not be construed to limit the present invention in any way.

The access port AP defines a tube or sheath SH with an inner lumen sized to receive various instruments that can enter and exit the cavity of the heart easily without creating unnecessary leakage. A modified expandable element 12' on the distal end of the sheath SH functions in a similar manner as the expandable element 12 on the end of the entry device 10 of FIGS. 1A-1C. In the embodiment of FIGS. 3A/3B the tubular cutter 20 is shown threaded over a relatively thin shaft 14, while in FIG. 5B a modified cutter element 20' travels over the larger diameter sheath SH.

As is illustrated in FIGS. 4A and 4B, access port AP also includes a bracing holder including a spring mechanism that is facilitated by a stop 34 (which serves as an anchoring element) and a grip element 30. Together, these two elements form a "stop-grip mechanism" that operates to brace or hold access port AP in one position. As used herein in this document, the term "stop-grip mechanism" connotes any component (e.g. spring loaded, friction-based systems, ratcheting configurations, etc.) that offers the ability to secure access port AP into a designated position. This feature allows increased freedom for the surgeon, who has been delegated to perform the surgery, as explained repeatedly herein. The term "grip element" refers to an element that contacts the exterior of the heart wall and provides a compressive reaction force in opposition to the force on the inner wall of the heart chamber provided by the expandable element 12'.

Specifically, applying pressure (i.e. a squeezing force) to the heart wall by these two components (expandable element 12' and grip element 30) causes a compression and then a subsequent resistive force, which secures access port AP in a specified position. This locking feature affords the aforementioned liberation to a surgeon who, while access port AP is stable, is able to perform other tasks while access port AP remains in its seated position. Thus, the present invention offers increased flexibility to the surgeon because it can seat and remain in its intended position, while the surgeon utilizes other medical instruments or performs other tasks. The present invention employs a spring mechanism that eliminates the need for a surgeon to constantly apply pressure in holding the device in a fixed position. Access port AP allows for an easy entry and exit from the sheath via a diaphragm, an elastomeric valve, or any other element that facilitates such movement.

With access port AP appropriately positioned and with the expandable member 12' deployed, a small amount of traction can be applied to the shaft in order to seat the expandable member against the interior wall of the heart. At this point, the surgeon can perform a simple thumb manipulation (e.g. a thumb wheel) to advance the exterior foot against the exterior surface of the heart. A simple spring can be provided to take up some amount of deflection of the wall thickness due to contraction of the heart muscle and, further, to provide a measure of safety against over compressing the heart muscle and, thereby, causing pressure necrosis. The thumb wheel can be advanced until the spring is partially or fully compressed; visual monitoring will allow the surgeon to see when the spring is fully compressed such that advancement is no longer required. From this point, the access port is installed and ready to use.

At the proximal end of device 10, a hemostatic valve can be used to allow devices to be placed and removed while minimizing blood loss. The valve uses two separate features for sealing. With no tool in place, a modified duckbill valve (or any other suitable valve system) can be used to provide the hemostatic effect. With a tool placed through the valve, a circumferential wiper seal can be used to allow the tool to be moved within the seal and to provide for a range of tool sizes to be accommodated.

To remove device 10, the thumb wheel (or any other suitable releasing mechanism) can be rotated to release tension of the foot against the outer heart surface. The inner rod 13 and outer shaft 14 can then be manipulated, relative to one another, to collapse expandable element 12'. Device 10 can then be gently withdrawn from the wall of the heart.

After device 10 is removed, the initial cut can be sutured to close the hole and, further, the hemostasis can then be verified.

Access port AP also desirably includes a sump element 40, which operates to release or exhaust air bubbles or other debris that is present in the system. Sump element 40 is removable.

At the proximal end, which generically represents the handle end of the instrument, access port AP includes a simple diaphragm or elastomeric valve V that offers the ability to receive and seal around objects passed through the access port AP. For example, as seen in FIG. 4B the valve V seals around shaft of obturator 18. In one embodiment, the valve is a window valve that is less cumbersome than conventional valves. However, access port AP could readily employ conventional valves, or any other type of conduit that could easily facilitate the teachings of the present invention, as outlined herein.

FIG. 4C illustrates how the bracing holder of access port AP is actuated when grip element 30 moves laterally toward the distal end of the instrument. Grip element 30 thus interfaces with the ventricular wall, whereby blood is properly sealed from leaking around access port AP. In addition, it should be noted that the obturator 18 and its shaft are removed in the embodiment of FIG. 4C to permit passage of instruments through the access port AP.

Figure 5F:
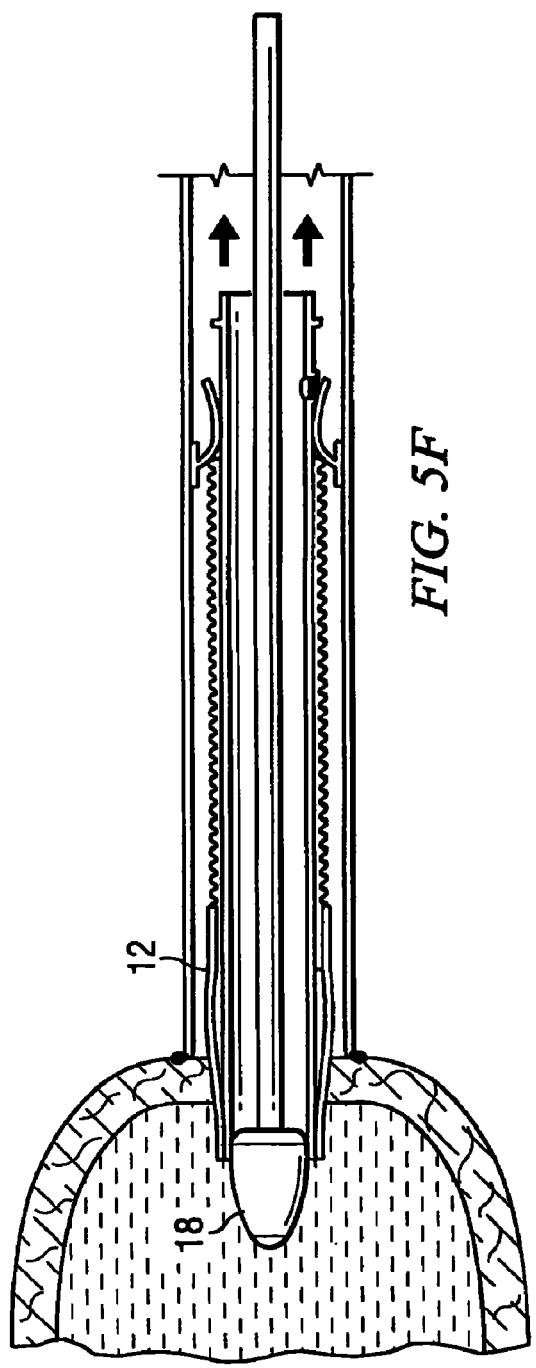

FIGS. 5A-G are simplified schematic diagrams of a top view of access port AP without the valve V and its housing (FIGS. 4A-4C). FIG. 5A illustrates access port AP with obturator 18 and shaft 14 inserted to provide an inner fluid seal therewithin. That is, the obturator 18 and shaft 14 may be inserted into access port AP to enable removal of the valve V and its housing. FIG. 5B illustrates access port AP with sump 40 removed and corresponding opening plugged, and a modified cutter element 20' positioned over the sheath SH. Based one set of particular design choices, the width of the modified cutter element 20' is about 18 millimeters and the shaft 14 is about 15 millimeters. Once again, the reader should be reminded that these measurements are only offered as examples, as any permutations or alternations in these specifications are clearly within the broad scope of the present invention.

FIG. 5C is a simplified schematic diagram of a top view of access port AP installed through the ventricular wall after a number of components have been removed. The removal of these components could be the result of a shift in objectives for the attending surgeon. As highlighted above, the surgeon is afforded the capability of abandoning the originally intended procedure in certain situations. For example and with reference to FIG. 5B, after a surgeon recognizes that he must change his strategy, the surgeon could reinsert the obturator 18, remove the valve V and valve housing, take off sump 40, and discard stop 34 and gripping element 30. The surgeon could then position cutter element 20' over the apparatus to allow for a circular cut to be made. In this instance, the cut will allow for a valve conduit 28 to be suitably positioned at the surgical site. The valve conduit can be slipped over the outside of the access port AP as seen in FIG. 5D and then fixed to the wall of the heart. Then, expandable element 12' can then be retracted and removed from within the valve conduit 28.

FIG. 5E illustrates a number of sutures S that are made at the ventricular wall. The sutures S are illustrated as small notches in this depiction. To facilitate the connection, the valve conduit 28 may possess a flared end that provides more suturing area. Furthermore, expandable element 12' can be shaped as a concave umbrella that does not contact the inner ventricle directly opposite the end of the valve conduit 28 such that a surgeon has ample room to perform appropriate suturing. In a sense, expandable element 12' could be provided with a lip that facilitates this operation. FIG. 5F illustrates expandable element 12' in its collapsed state such that it can be removed from the surgical site.

Figure 5G:
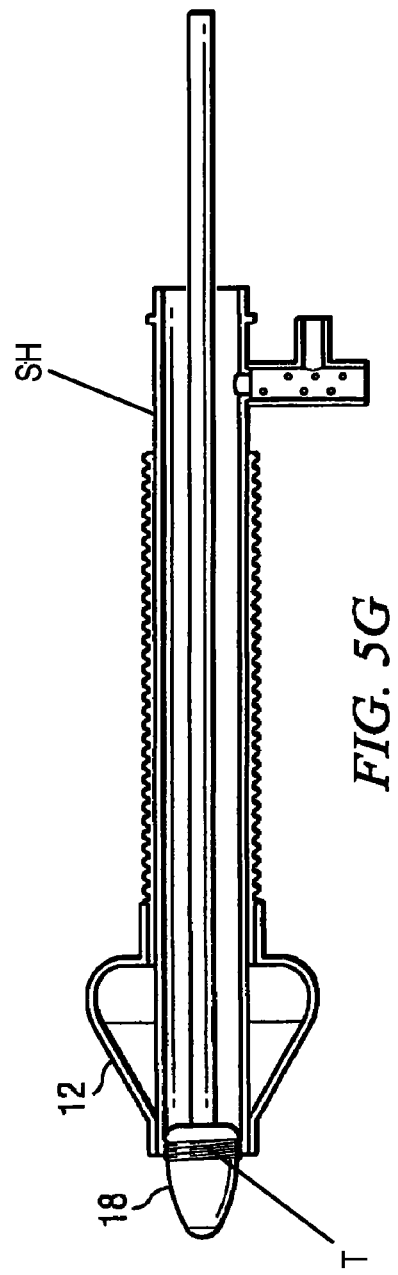

FIG. 5G illustrates an alternative embodiment of the present invention. In this embodiment, obturator 18 is fitted with threads T such that it can be removed from, or secured to, an inner wall of the sheath SH to create an appropriate seal. In such a scenario, there are two sheaths (or tubes) present that allow for a number of components to be removed without breaking the seal.

In operation of another example embodiment used to illustrate some of the applications of the present invention, consider the case of a patient who is experiencing some pain that emanates from the left side of their heart or the pumping chamber generally. The pathology of the patient could be simple stenosis or it could involve atrial fibrillation, a cardiac tumor, etc. In other instances, the patient could require a change in the shape of the ventricle itself by remodeling, sewing, placating, or by placing a patch in a targeted area. All of these issues require the surgeon to have access to the inside of the ventricle.

As an initial step, the surgeon may use access port AP in creating a small hole in the apex of the heart. Expandable element 12' occupies part of the ventricle because of its shape and because the tissue is somewhat malleable. Hence, when a somewhat rigid expandable element 12' is pulled against this tissue, a viable seal is created. Once the seal has been created, other components of access port AP can be utilized on the other side of expandable element 12' to essentially squeeze the wall and to lock access port AP into a specific position. Now, the access device can be dropped or unhanded such that the surgeon can focus on other tasks at hand without having to hold access port AP. This shift in emphasis, from focusing on maintaining a fixed position of an instrument to concentrating on the procedure itself, is critical to the success of any medical procedure. By employing access port AP, the surgeon is no longer burdened with menial or tedious chores; instead, his attention is on the surgery itself. Note that access port AP allows access to the intracardiac chamber without entraining air and without dropping removed portions of tissue. Further, access port AP allows the surgeon to use other instruments while in the chamber (e.g. forceps, a laser, a scope or other visualization instrument, etc.).

Another important advantage offered by access port AP is that it affords the surgeon the ability to always have a "completed procedure." For example, if for some reason the objectives of the surgeon are not being met during the initial surgery, he can simply shift his strategy, place a valve conduit at the surgical site, and necessarily resolve this patient in some fashion: even if resolution involves a strategy that was different from the originally intended objective. This is in contrast to other, more limited systems and devices that offer an all-or-nothing proposition. Consider the case of a simple stent procedure that, for some arbitrary reason, goes awry. While in a catheter laboratory, the surgeon cannot avail himself to alternative surgical options. Hence, these stent procedures are not amenable to any shift in operational strategy. However, access port AP is adaptive, as some of its components can easily be manipulated to achieve objectives that are different from those originally proposed.

Note that any of the previously discussed materials could be included in a given kit, which could ostensibly be provided to a surgeon who is responsible for performing a cardiovascular procedure. A basic kit could include entry device 10, along with an accompanying access port AP and a valve V to be used in conjunction therewith. Any of these components may be manufactured based on particular specifications or specific patient needs. The present invention contemplates considerable flexibility in such components, as any permutation or modification to any of these elements is clearly within the broad scope of the present invention.

It is important to note that the stages and steps in the preceding FIGURES illustrate only some of the possible scenarios that may be executed by, or within, the architecture of the present invention. Some of these stages and/or steps may be deleted or removed where appropriate, or these stages and/or steps may be modified or changed considerably without departing from the scope of the present invention. In addition, a number of these operations have been described as being executed concurrently with, or in parallel to, one or more additional operations. However, the timing of these operations may be altered considerably. The preceding example flows have been offered for purposes of teaching and discussion. Substantial flexibility is provided by the proffered invention in that any suitable arrangements, chronologies, configurations, and timing mechanisms may be provided without departing from the broad scope of the present invention.

Note also that the example embodiments described above can be replaced with a number of potential alternatives where appropriate. The processes and configurations discussed herein only offer some of the numerous potential applications of the device of the present invention. The elements and operations listed in FIGS. 1A-5C may be achieved with use of the present invention in any number of contexts and applications. Accordingly, suitable infrastructure may be included within device 10 or access port AP (or cooperate therewith) to effectuate the tasks and operations of the elements and activities associated with managing a bypass procedure.

Although the present invention has been described in detail with reference to particular embodiments in FIGS. 1A-5C, it should be understood that various other changes, substitutions, and alterations may be made hereto without departing from the sphere and scope of the present invention. For example, although the preceding FIGURES have referenced a number of components as participating in the numerous outlined procedures, any suitable equipment or relevant tools may be readily substituted for such elements and, similarly, benefit from the teachings of the present invention. These may be identified on a case-by-case basis, whereby a certain patient may present a health risk factor while another (with the same condition) may not. Hence, the present device may be designed based on particular needs with particular scenarios envisioned.

It is also imperative to note that although the present invention has been illustrated as implicating a procedure related to the apex of the heart, this has only been done for purposes of example. The present invention could readily be used in any cardiovascular procedure and, accordingly, should be construed as such. For example, the present invention can be used in applications involving the stomach, bladder, colon, bowels, etc. The present invention may easily be used to provide a viable vascular management solution at various locations of the mammalian anatomy, which are not necessarily illustrated by the preceding FIGURES.

Numerous other changes, substitutions, variations, alterations, and modifications may be ascertained to one skilled in the art and it is intended that the present invention encompass all such changes, substitutions, variations, alterations, and modifications as falling within the spirit and scope of the appended claims. In order to assist the United States Patent and Trademark Office (USPTO) and additionally any readers of any patent issued on this application in interpreting the claims appended hereto, Applicant wishes to note that the Applicant: (a) does not intend any of the appended claims to invoke paragraph six (6) of 35 U.S.C. section 112 as it exists on the date of filing hereof unless the words "means for" are specifically used in the particular claims; and (b) does not intend by any statement in the specification to limit his invention in any way that is not otherwise reflected in the appended claims.

What is claimed is:

1. An access port to allow sealed access through a wall of the heart during a beating heart cardiac procedure, comprising;
   an elongated tubular sheath having a proximal end, a distal end, and a lumen extending therebetween;
   a single expandable element on the tubular sheath, the expandable element being disposed around the distal-most end of the sheath and having a compressed state and an expanded state, wherein the expandable element is operable to be positioned within a chamber of the heart while in the compressed state, and wherein the expandable element is further operable to be deployed once it is within the heart chamber to convert to the expanded state and contact an interior wall of the heart chamber;
   a stop-grip mechanism disposed on the exterior of the sheath proximal to the expandable element including a grip member axially movable over the sheath and adapted to contact an exterior wall of the heart chamber and apply a compressive force across the wall in opposition to the expandable element in its expanded state, and a variable position stop member positioned proximal to the grip member and adapted to apply a distal bias to the grip member, wherein the grip member slides freely along the sheath, and the stop member is internally-threaded and controllably movable along external threads on the sheath, and the stop-grip mechanism further includes a spring mechanism in between the grip member and stop member that provides the compressive force; and
   a device valve connected to the proximal end of the sheath to allow devices to be placed and removed through the sheath while minimizing blood loss.

2. The access port of claim 1, wherein the device valve includes both a hemostatic valve that closes when no devices are present and a wiper seal that seals around a range of device sizes.

3. The access port of claim 1, further comprising an obturator on the distal end of a shaft, the obturator being sized to form a seal with the inner lumen of the sheath.

4. The access port of claim 1, further comprising a sump element on a proximal end of the sheath which operates to exhaust air bubbles present in the sheath.

5. The access port of claim 1, wherein the device valve is removable from the sheath, and further including a tubular cutter for forming a circular incision sized to pass along the exterior of the sheath to the heart chamber wall.

6. The access port of claim 5, further including mating threads provided on the exterior of the sheath and on the interior of the cutter.

7. The access port of claim 1, wherein the device is sized to allow a sealed access to the left ventricle of a patient for placement, manipulation, or repair of a heart valve through the sheath lumen.

8. The access port of claim 1, wherein the expandable element is a braided structure.

9. The access port of claim 8, wherein the braided structure is coated with an elastomeric membrane.

10. The access port of claim 8, wherein the braided structure is expanded by applying linear compression thereto.

11. An access port to allow sealed access through a wall of the heart during a beating heart cardiac procedure, comprising;
    an elongated tubular sheath having a proximal end, a distal end, and a lumen extending therebetween, the sheath having external threads;
    an expandable element disposed around the distal end of the sheath having a compressed state and an expanded state, wherein the expandable element is operable to be positioned within a chamber of the heart while in the compressed state, and wherein the expandable element is further operable to be deployed once it is within the heart chamber to convert to the expanded state;
    a sealing mechanism disposed on the exterior of the sheath proximal to the expandable element including a grip member axially movable over the sheath and adapted to apply a compressive force across a wall of the heart chamber in opposition to the expandable element in its expanded state;
    a device valve connected to the proximal end of the sheath to allow devices to be placed and removed through the sheath while minimizing blood loss; and
    a tubular cutter having internal threads and sized to advance along the external threads of the sheath to the heart chamber wall, the cutter having a sharp end for forming a circular incision in the heart chamber wall.

12. The access port of claim 11, wherein the tubular cutter is smaller than the expandable element in its expanded state.

13. The access port of claim 11, wherein the tubular cutter is hollow or concave such that it can incise and retain a circular portion of tissue.

14. The access port of claim 11, wherein the device valve includes both a hemostatic valve that closes when no devices are present and a wiper seal that seals around a range of device sizes.

15. The access port of claim 11, further comprising an obturator on the distal end of a shaft, the obturator being sized to form a seal with the inner lumen of the sheath.

16. The access port of claim 11, wherein the device valve is removable from the sheath to permit the tubular cutter to pass along the exterior of the sheath to the heart chamber wall.

17. The access port of claim 11, wherein the grip member slides freely along the sheath, and wherein the sealing mechanism includes an internally-threaded stop member positioned proximal to the grip member and controllably movable along the external threads on the sheath, and a spring mechanism in between the grip member and stop member that provides the compressive force.

18. The access port of claim 11, wherein the device is sized to allow a sealed access to the left ventricle of a patient for placement of a heart valve through the sheath lumen.

19. The access port of claim 11, wherein the expandable element is a braided structure.

\* \* \* \* \*